United States Patent [19]
Yoon et al.

[11] Patent Number: 6,071,734
[45] Date of Patent: Jun. 6, 2000

[54] HBV POLYMERASE, RNASE H ENZYME DERIVED FROM HBV POLYMERASE, PROCESSES FOR PREPARATION AND USES FOR SCREENING ANTIVIRAL AGENTS THEREOF

[75] Inventors: Sung-June Yoon, Seoul; Jong-Woo Kim, Anyang-si; Yong Huh, Kunpo-si; Hyune-Mo Rho, Socho-ku; Gu-Hung Jung, Seoul, all of Rep. of Korea

[73] Assignee: Dong Wha Pharm. Ind. Co., Ltd., Seoul, Rep. of Korea

[21] Appl. No.: 09/228,243

[22] Filed: Jan. 11, 1999

Related U.S. Application Data

[62] Division of application No. 08/911,774, Aug. 15, 1997, Pat. No. 5,968,781.

[30] Foreign Application Priority Data

Aug. 16, 1996 [KR] Rep. of Korea ...................... 96-33998
Dec. 9, 1996 [KR] Rep. of Korea ...................... 96-63255

[51] Int. Cl.$^7$ .............................. C12N 9/22; C12N 1/20; C12N 15/00; C12N 5/00; C12P 21/04
[52] U.S. Cl. .................... 435/199; 435/69.7; 435/252.3; 435/254.11; 435/320.1; 435/325; 435/410
[58] Field of Search .................................. 435/69.7, 199, 435/252.3, 254.11, 320.1, 325, 410

[56] References Cited

PUBLICATIONS

Müller et al., "Co–expression of the Subunits of Heterodimer of HIV–1 Reverse Transcriptase in *Escherichia coli*", J. Bio. Chem 264, No. 24, pp. 13975–13976 (Aug. 1989).

Tan et al., "Inhibition of the RNase H Activity of HIV Reverse Transcriptase by Azidothymidylate", Biochemistry 30, No. 20, pp. 4831–4835 (May 1991).

Smith et al., "Purification and Characterization of Active Human Immunodeficiency Virus Type 1 RNase H Domain", Journal of Virology 67, No. 7, pp. 4037–4049 (Jul. 1993).

*Primary Examiner*—Robert A. Wax
*Assistant Examiner*—Einar Stole
*Attorney, Agent, or Firm*—Dilworth & Barrese

[57] ABSTRACT

The present invention relates to hepatitis B virus (hereinafter it refers to HBV) polymerase containing a histidine tag, RNase H enzyme derived from HBV polymerase and processes for preparation thereof. More particularly, the present invention relates to recombinant HBV polymerase, its RNase H domain with enzyme activity, expression vectors producing the enzymes in *E. coli* and processes for preparing the HBV polymerase and the RNase H enzyme which can be easily purified due to their histidine tags. And the present invention relates to uses of the HBV polymerase and the RNase H enzyme for screening antiviral agents.

10 Claims, 15 Drawing Sheets

0   0.1 0.2 0.4 0.8 1.6
amount of protein (μg)

HBV POLYMERASE, RNASE H ENZYME DERIVED FROM HBV POLYMERASE, PROCESSES FOR PREPARATION AND USES FOR SCREENING ANTIVIRAL AGENTS THEREOF

This application is a divisional of application Ser. No. 08/911,774 filed Aug. 15, 1997 now U.S. Pat. No. 5,968,781.

BACKGROUND OF THE INVENTION

Field of the Invention

The present invention relates to hepatitis B virus (hereinafter it refers to HBV) polymerase containing a histidine tag, RNase H enzyme derived from HBV polymerase and processes for preparation thereof.

More particularly, the present invention relates to recombinant HBV polymerase, its RNase H domain with enzyme activity, expression vectors producing the enzymes in E. coli and processes for preparing the HBV polymerase and the RNase H enzyme which can be easily purified due to their histidine tags.

And the present invention relates to uses of the HBV polymerase and the RNase H enzyme for screening antiviral agents.

HBV is the main virus among hepatitis viruses, which infects more than 300 million people worldwide. HBV causes acute or chronic hepatitis, which results in liver cirrhosis or liver cancer (Tiollais and Buenda, Scientific American, 264: 48–54, 1991 ; Blumberg, B. S., Background and perspective in advances in hepatitis research, F. V. Chisari, ed., New York, Mason publishing, 1984). Because of molecular characteristics of HBV and its close relation with liver diseases, various researches about HBV have been accomplished.

HBV is a DNA virus, a member of the hepadnaviridae family, which has a spherical structure composed of nucleocapsid and core. HBV genome is a partially double stranded DNA of only 3.2 kb size, which is not a circular form. In detail, HBV genome is composed of four overlapped genes that are the polymerase (P) gene, the surface protein (HBsAg; S, pre-S1, pre-S2) gene, the core protein (HBcAg; pre-C, C) gene and X protein (HBx) gene. Among these genes, X protein gene encodes regulatory protein, and the other genes encode structural proteins of HBV. The polymerase gene occupies 80% of the total genome and encodes 94 KD-sized protein composed of 845 amino acids.

HBV infects hepatic cells by the process described below. The specific receptor of the hepatic cell recognizes the surface protein on the surface of the virion particle and binds with them so as to draw the virion into the hepatic cell. Then HBV polymerase synthesizes the single-stranded part of partially double-stranded DNA in order to obtain complete HBV genome. And the HBV genome of 3.2 kb size is transcribed with cellular RNA polymerase to produce pre-genomic mRNA of about 3.5 kb, core protein (C) mRNA, surface protein mRNA and X protein mRNA. Viral proteins are translated from these mRNAs. Specially HBV polymerase synthesizes an RNA intermediate with its reverse transcriptase activity so as to provide a template for the DNA genome and make a replicasome structure with the pre-genomic mRNA, the core protein and the like, which is called encapsidation process. The HBV genome can be encapsidated easily since 3'-terminus of the polymerase containing continuous glutamic acid residues has affinity with nucleic acids. The above RNA intermediate in the replicasome serves as a template for minus strand DNA synthesis and then the full-length minus strand serves as a template for plus strand DNA synthesis by DNA-dependent DNA polymerase (DDDP) activity of the polymerase so as to make total pre-genomic mRNAs finally. By repeating the above process, more than 200–300 copies of the genomic DNA is maintained in pool and the viral proteins mentioned above are expressed (Tiollais and Buenda, Scientific American, 264: 48–54, 1991 ; Ganem, D. and Varmus, H. E., Annu. Rev. Biochem., 56: 651–693, 1987).

Interestingly, HBV replicates its genome by using the RNA intermediate and reverse transcription even though it is a DNA virus. It is-known that retrovirus exploits the reverse transcription to replicate its genome. Particularly, the polymerase of retrovirus is reported to be a multifunctional enzyme which shows DNA-dependent DNA polymerase activity, reverse transcriptase activity, and RNase H activity. It is remarkable that HBV polymerase contains a series of functions necessary for the replication of virus genome. Namely, the following functions: (i) protein primer, (ii) RNA-dependent DNA polymerase (RT), (iii) DNA-dependent DNA polymerase (DDDP), (iv) RNase H activity consist in one polypeptide. The reverse transcriptase activity of HBV polymerase was first reported by Kaplan et al., and has been exploited to elucidate the mecahnism of HBV replication.

As mentioned above, a reverse transcriptase has an active RNase H domain commonly which recognizes RNA/DNA complex and hydrolyzes only the RNA strand selectively. The RNase H activity is indispensable to the reverse transcription, since the reverse transcriptase can replicate DNA continuously only after RNA intermediate is hydrolyzed by the RNase H activity. Although RNase H enzyme is known as a domain of the reverse transcriptase recently, RNase H enzyme was first discovered in the calf thymus by Hausen and Stein, and has been reported from various prokaryotes and eukaryotes (Stein, Hans and Hausen, P., Science, 166 393–395, 1969).

Generally speaking, an active RNase H domain of HBV polymerase is localized within its C-terminus. The amino acid sequence and nucleotide sequence of the polymerase were reported to be very similar to those of the polymerase of Moloney murine Leukemia Virus. In addition, an active RNase H domain of HBV polymerase was known to synthesize a plus strand primer which can be derived from the pre-genomic RNA putatively. Particularly, it was identified by performing mutagenesis that the conserved sequence in the RNase H enzyme was necessary for viral proliferation. In addition, the RNase H domain plays a role to synthesize a minus strand DNA as well as the plus strand DNA and to perform RNA packaging, which is identified by mutating the RNase H domain of duck HBV polymerase. But it is reported recently that duck HBV polymerase can not recognize binding region E within the pre-genomic RNA of human HBV.

Therefore, human HBV polymerase and its RNase H domain should be studied directly in addition to indirect researches by utilizing duck HBV polymerase in order to elucidate human HBV and the mechanism of its polymerase. Hitherto, the surface protein and the X protein which is necessary for the development of vaccines and for the regulation of transcription in proceeding liver cancer respectively has been studied actively. However, HBV polymerase has seldom been exploited although it can be used to develop antiviral agents. Because HBV polymerase is difficult to be separated from virus particle and to obtain sufficient amounts, especially as an active form (Radziwill, G. et al., Virology, 163: 123–132, 1988). Presently, in order to develop novel therapeutical agents for hepatitis, cell lines infected with HBV have been used for screening antiviral agents. However, effective therapeutical agents has not been yet developed, since it takes longer time and costs more for a screening method using cell lines than for screening methods using HBV polymerase or its RNase H enzyme.

Recently in order to elucidate HBV, HBV polymerase and its RNase H domain have been studied as descibed above. Particularly researches for the mass production of above enzymes have been attempted by using recombinant DNA technology. The inventors of the present invention have produced a recombinant HBV polymerase which is expressed from *E. coli* transformant, measured its enzyme activity and filed a patent application thereof (Korean Patent Application 94-3918). The recombinant HBV polymerase was produced in *E. coli* as a form of fusion protein with maltose binding protein (MBP), and can be easily purified by MBP affinity column chromatography. But active HBV polymerase is difficult to be obtained massively because the polymerase can be degradaded at the C-terminus and has low purity.

Foreign proteins can be obtained massively by inserting a histidine tag into the proteins by recombinant DNA technology. The nucleotide sequences encoding histidine tag is inserted into the 5'-terminus or 3'-terminus of the gene, and the histidine-tag prevents degradation of the recombinant protein so as to prepare stable enzyme. In addition, the highly active recombinant protein can be purified easily by using histidine tag affinity column as a metal chelating affinity column.

In order to develop effective therapeutical agents, HBV polymerase and its RNase H enzyme have been produced by processes of the present invention. The inventors constructed expression vectors containing HBV polymerase gene with nucleotide sequences encoding a histidine tag at the C-terminus of the recombinant protein and expression vectors containing RNase H domain gene which is derived from the 3'-terminus of the HBV polymerase gene. In addition, HBV polymerase and its RNase H domain have been produced as forms of fusion protein massively in *E. coli* by using the expression vectors and purified easily by using amylose column and histidine tag affinity column. Thus highly active and stable HBV polymerase and its RNase H enzyme which are not degradaded can be prepared. Furthermore, the inventors have developed novel screening methods for antiviral agents by using the HBV polymerase and its RNase H domain of the present invention.

SUMMARY OF THE INVENTION

The object of the present invention is to provide HBV polymerase containing a histidine tag, RNase H enzyme derived from HBV polymerase and processes for preparation thereof.

Particularly, the present invention provides expression vectors containing the HBV polymerase gene and process for preparing the HBV polymerase in *Escherichia coli*.

In addition, the present invention provides expression vectors containing RNase H gene derived from human HBV polymerase gene and process for preparing the RNase H enzyme in *Escherichia coli*.

And, the object of the present invention is to provide uses of the HBV polymerase and the RNase H enzyme for screening antiviral agents.

Particularly, the present invention provides methods for screening inhibitors of the HBV polymerase and the RNase H enzyme.

BRIEF DESCRIPTION OF THE DRAWINGS

lane 1: the HBV polymerase purified primarily by amylose column lane 2: the HBV polymerase purified secondarily by histidine tag affinity column

Figure 6A:
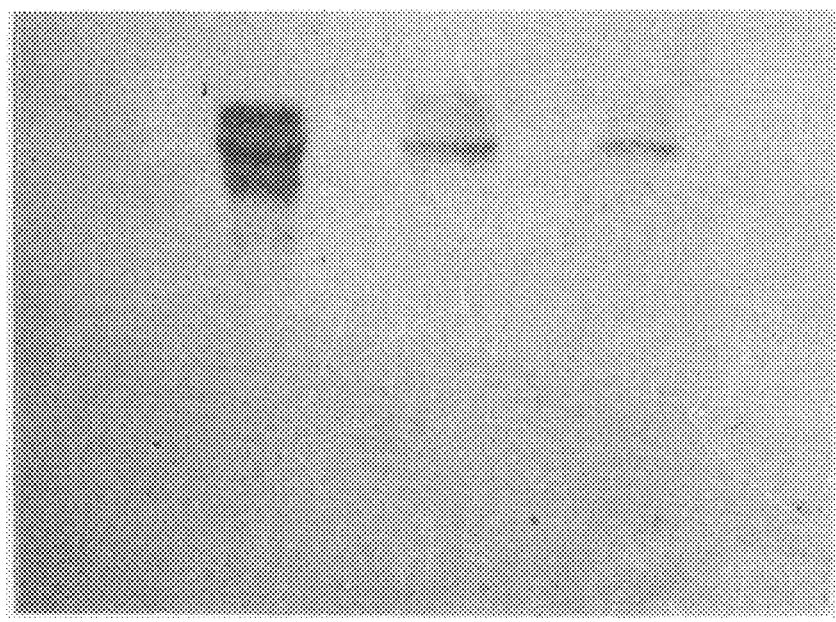
Figure 6B:
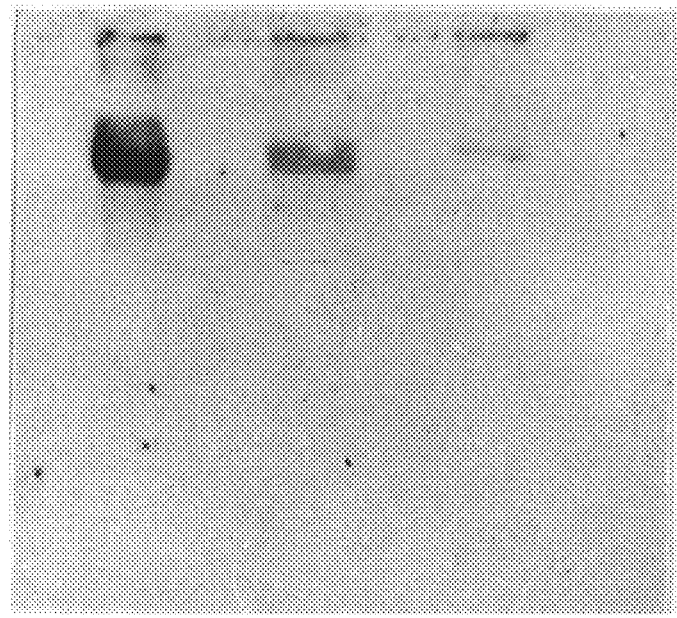

lane 1: standard marker (molecular weight is 97, 68, 43 and 29 KD respectively);

lane 2 crude extract of *E. coli* transformant lane 3: the RNase H enzyme purified primarily by amylose column lane 4: the RNase H enzyme purified secondarily by histidine tag affinity column FIG. 6 depicts the RNase H enzyme which has been produced and purified from the *E. coli* NM522 /pMRH transformant by western blotting analysis.

A: a result using anti-maltose binding protein

B: a result using antibody against histidine tag ($^{MRGS}$HIS)

Figure 5:
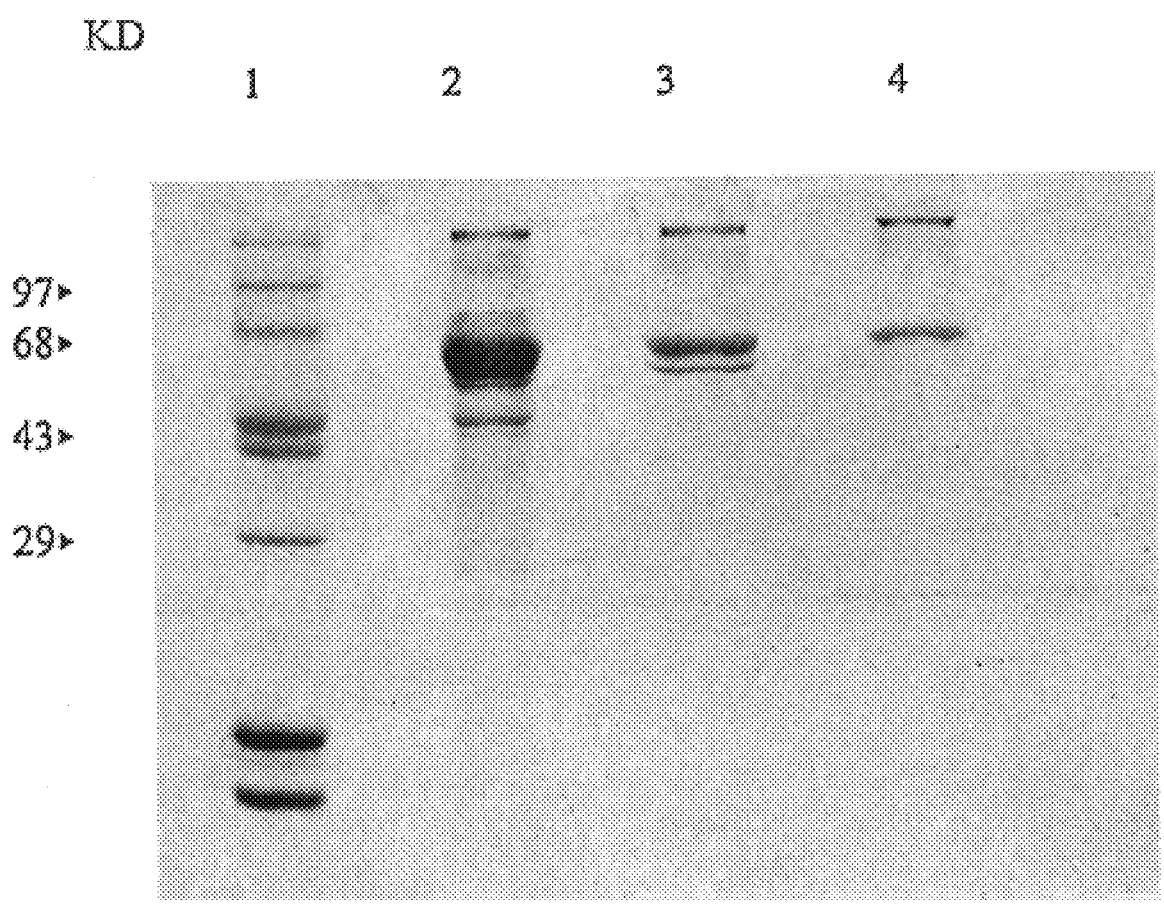
FIG. 5 depicts the RNase H enzyme which has been produced and purified from the *E. coli* NM 522/pMRH by SDS-polyacrylamide gel electrophoresis.

Each lane is explained on the above FIG. 5

Figure 7:
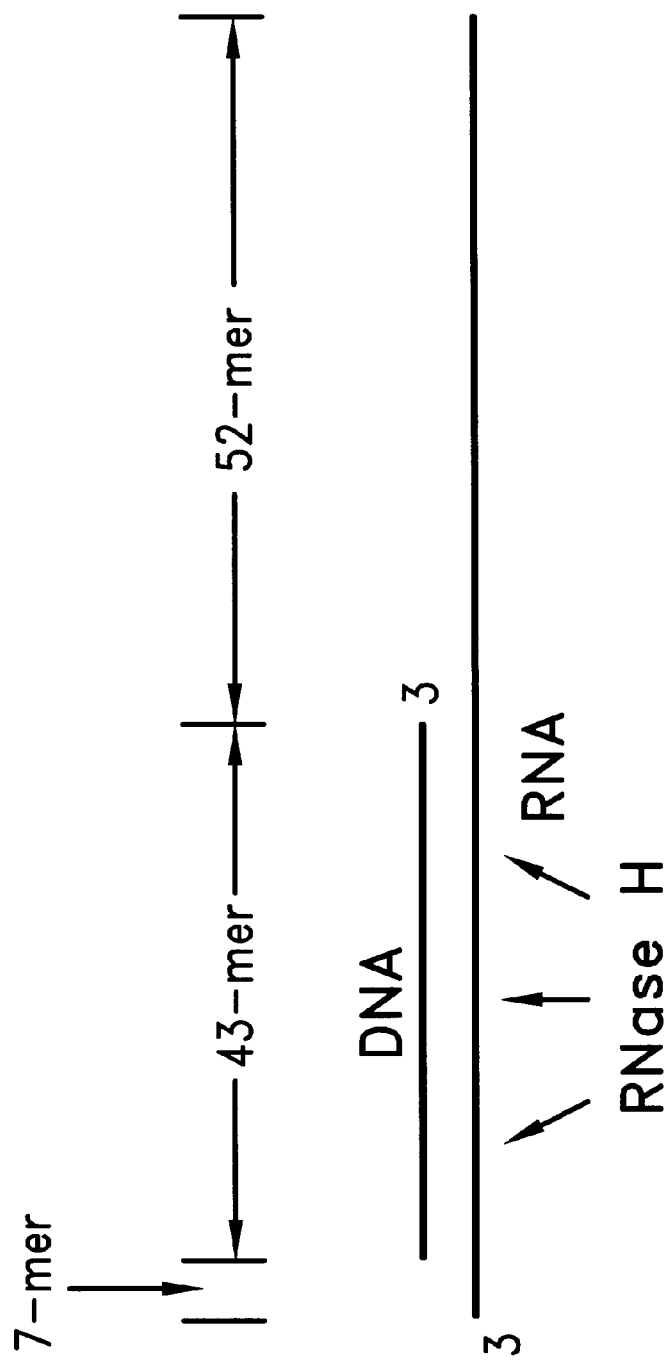

FIG. 7 depicts RNA/DNA complex used in assaying the RNase H activity of the present invention.

Figure 8:
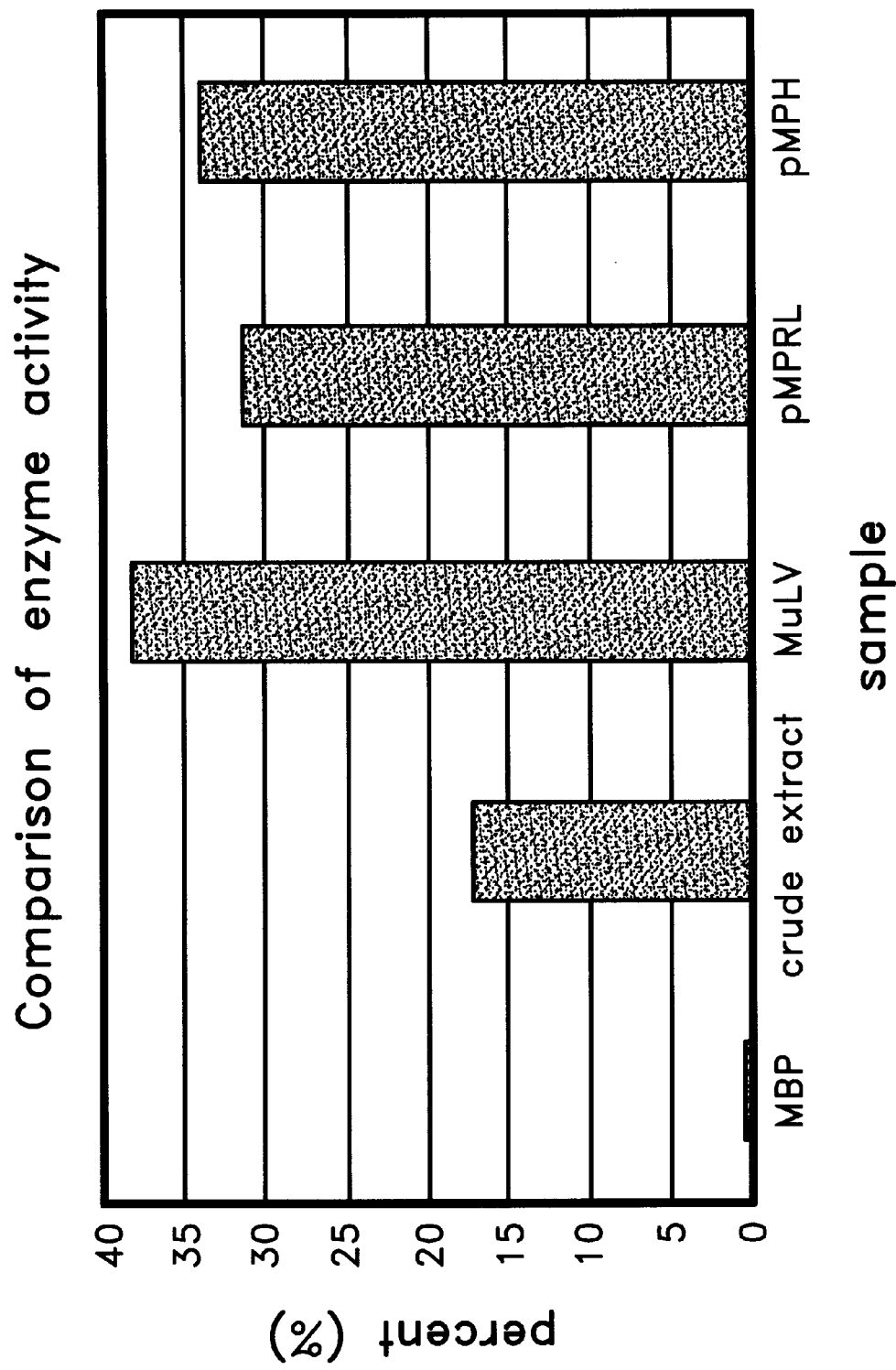
Figure 9:
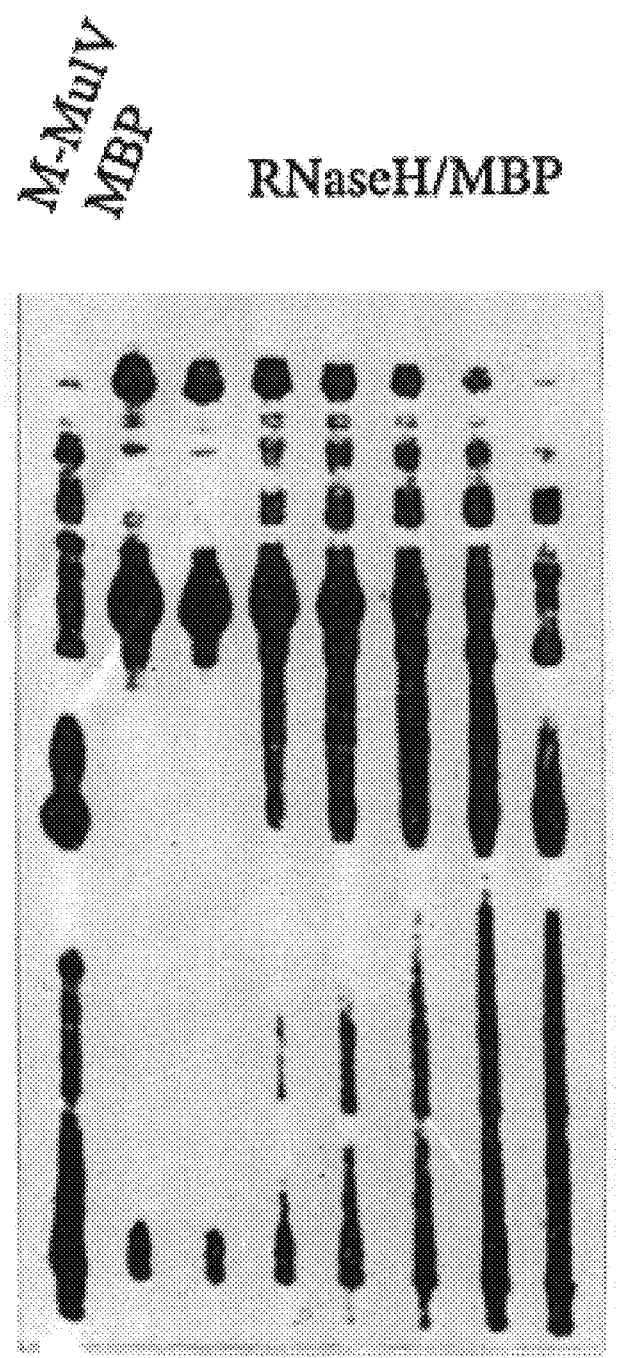

FIG. 8 represents the results comparing RNase H activities of following samples, (i) maltose binding protein, (ii) crude extract of the *E. coli* transformant cultured, (iii) the RNase H expressed and purified by using the expression vector PMPRL and amylose column, (iv) the RNase H expressed and purified by using the expression vector PMRH and amylose column, histidine affinity column, (v) reverse transcriptase of Moloney murine Leukemia Virus FIG. 9 represents the increase of the RNase H activity according to the amount of the RNase H enzyme.

Figure 10:
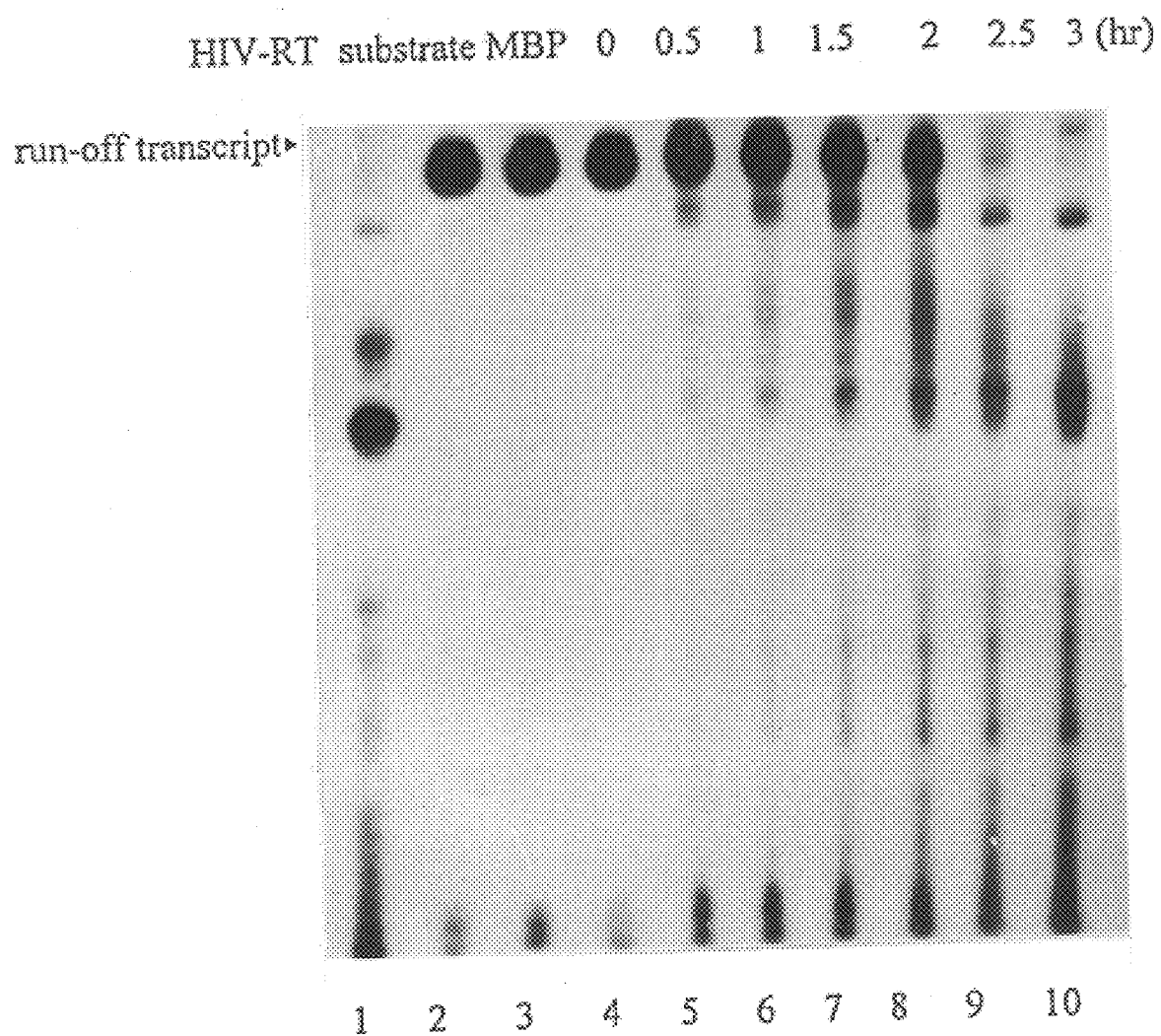

FIG. 10 represents the increase of the RNase H activity according to the reaction period of the RNase H enzyme.

Figure 11:
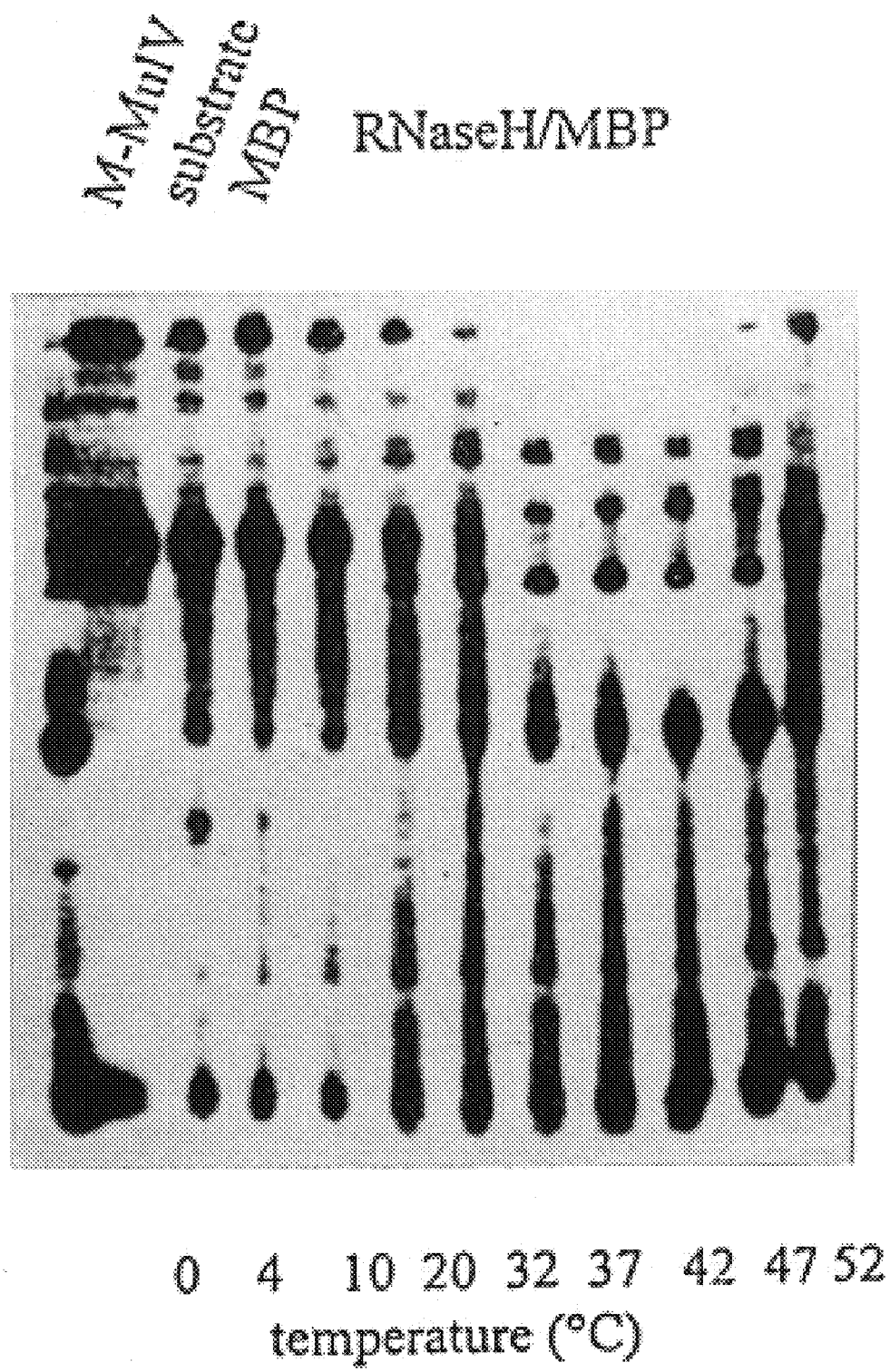

FIG. 11 represents the variation of the RNase H activity according to the reaction temperature.

Figure 12:
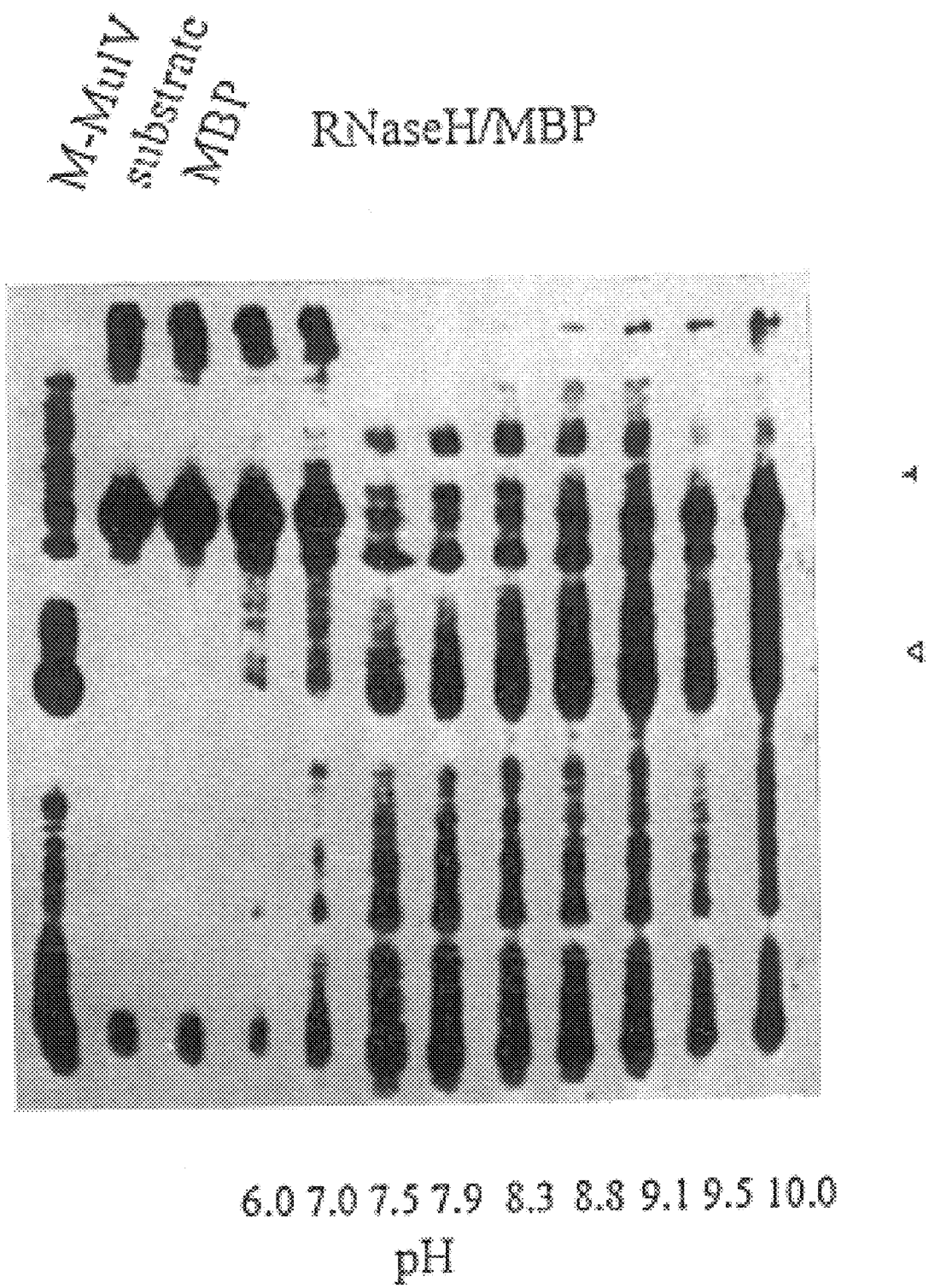

FIG. 12 represents the variation of the RNase H activity according to the pH of the reaction solution.

Figure 13:
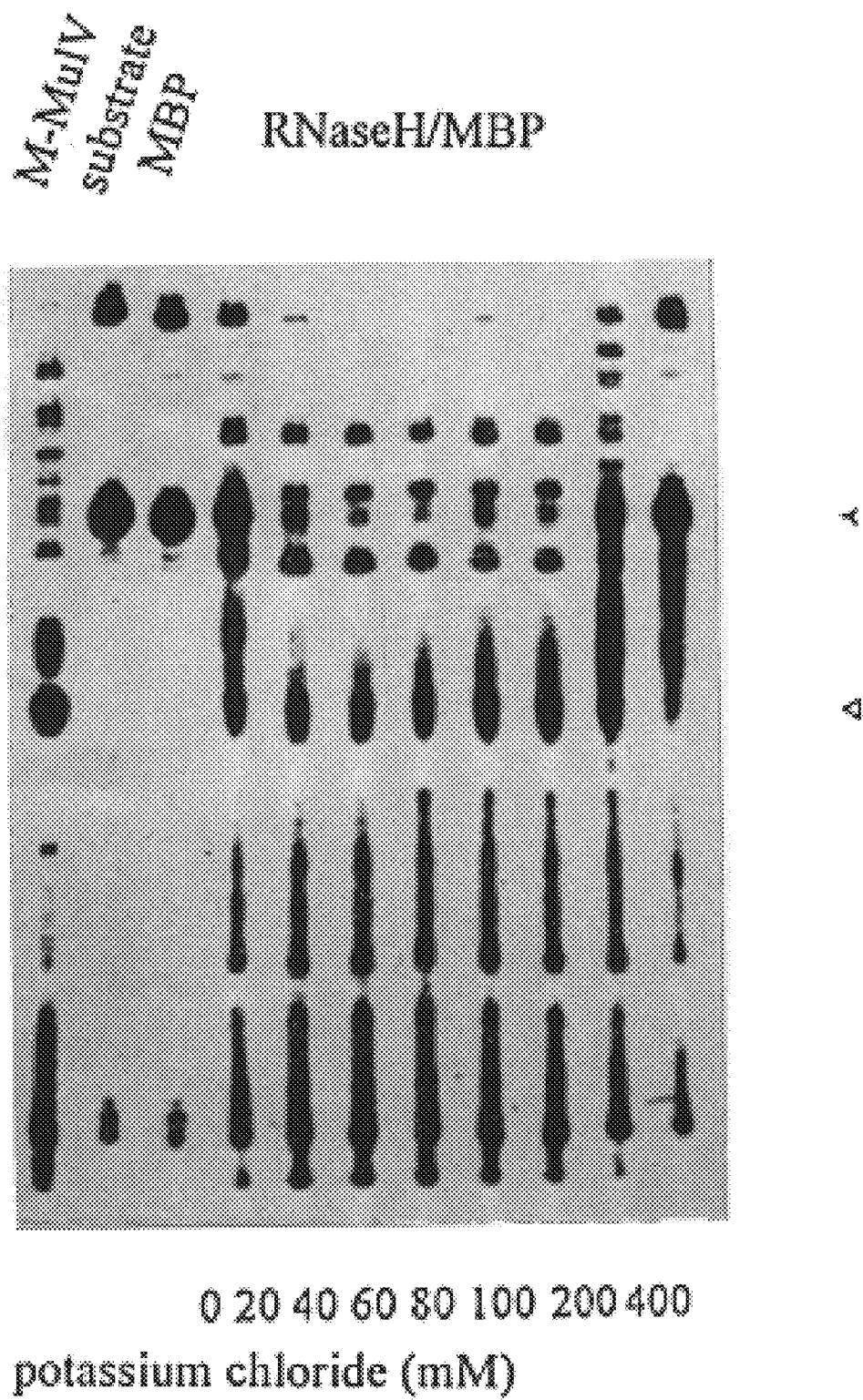

FIG. 13 represents the variation of the RNase H activity according to the concentration of potassium chloride.

Figure 14:
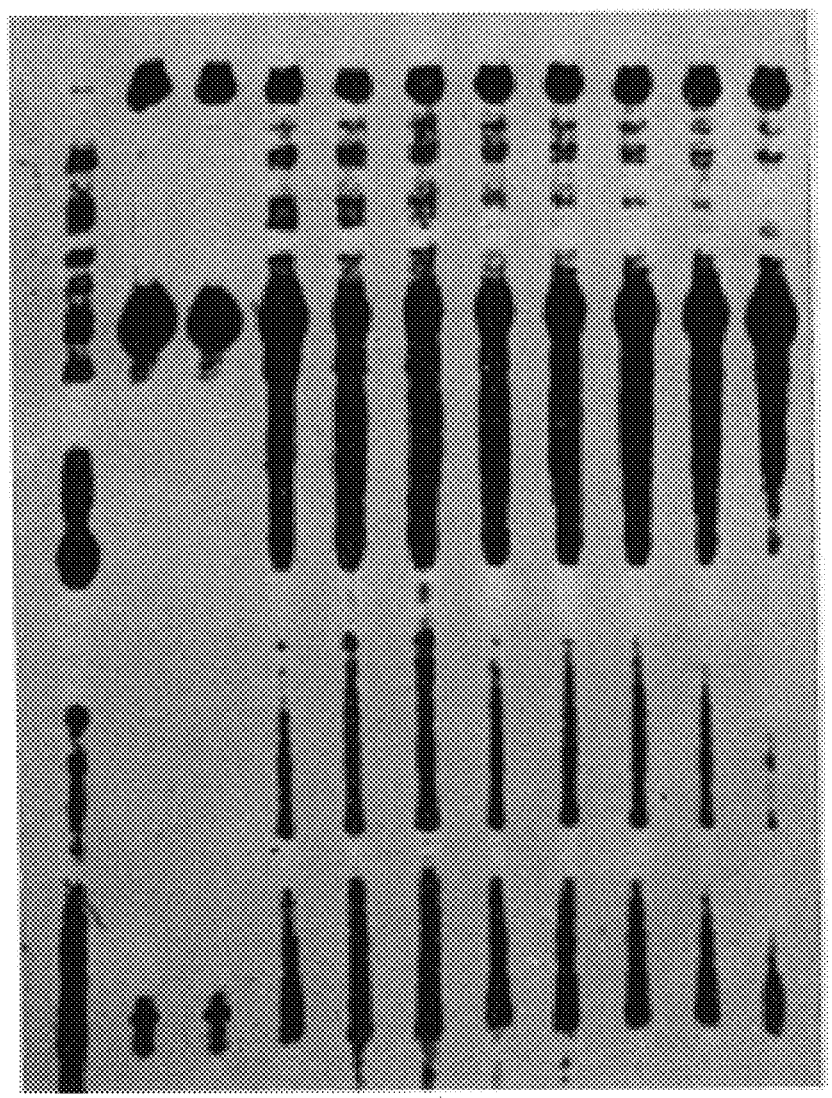

FIG. 14 represents the variation of the RNase H activity according to the concentration of magnesium ion.

Figure 15:
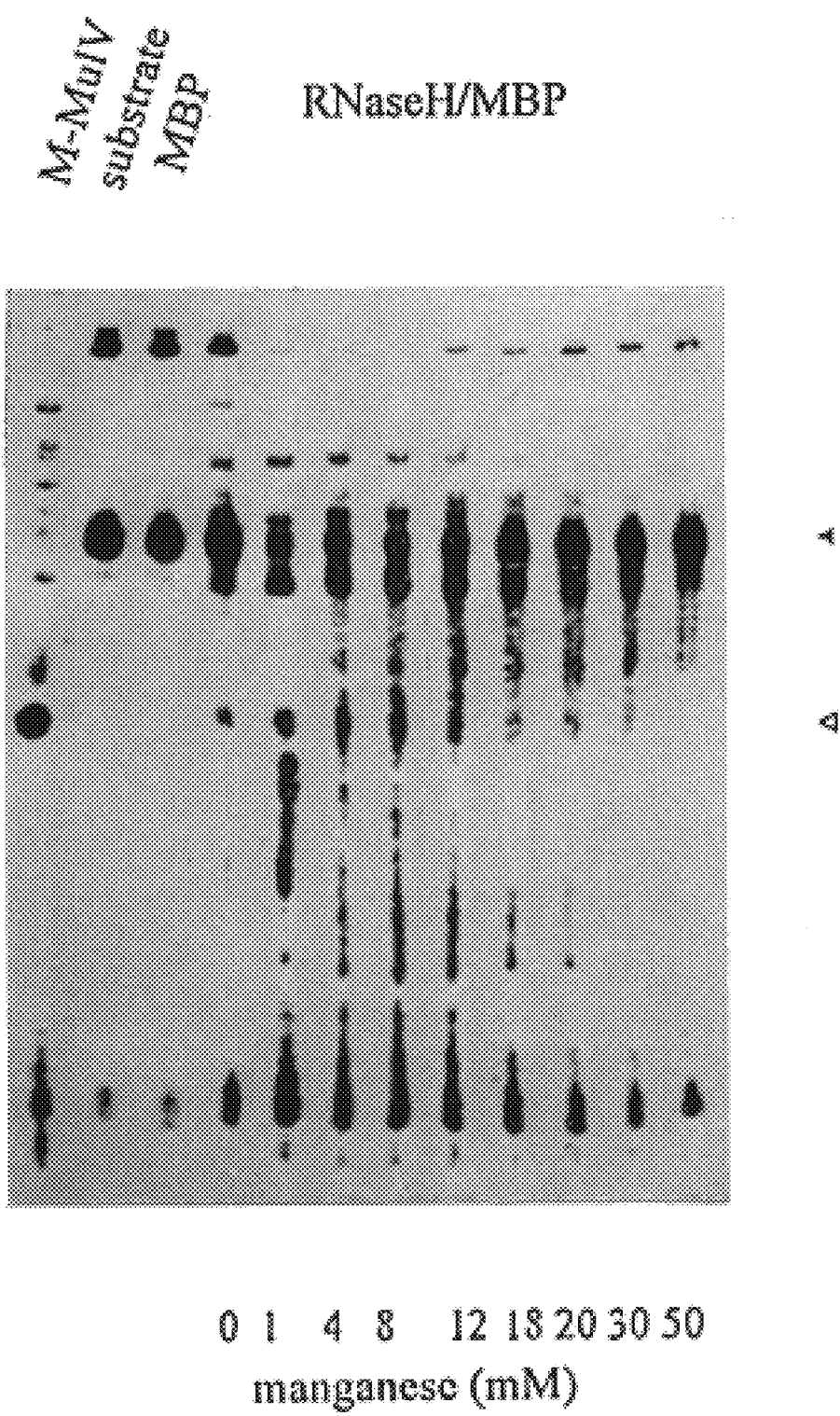

FIG. 15 represents the variation of the RNase H activity according to the concentration of manganese ion.

DETAILED DESCRIPTION OF THE PREFERRED EMBODIMENTS

The present invention provides HBV polymerase containing a histidine tag which is prepared by inserting nucleotide sequences of the histidine tag into the end of HBV polymerase gene.

Since the HBV polymerase containing a histidine tag is stable and can be easily purified, its activity of reverse transcriptase and the like can be measured properly. By using site-specific insertion mutagenesis and so on, nucleotide sequences of histidine tag can be inserted into 5'-terminus or 3'-terminus of the HBV polymerase gene.

Particularly, the present invention has exploited the expression vector already established (Korean Patent Application 94-3918) which produces the HBV polymerase fused with maltose binding protein (MBP). And nucleotide sequence of 6 histidine residues is inserted into the 3'-terminus of HBV polymerase gene. Especially since the histidine codons are inserted continuously right before the stop codon, the open reading frame (ORF) of the HBV polymerase gene is setted exactly. The histidine tag can be inserted into the C-terminus of the polymerase, which maintains the enzyme activity. As a result, the expression vector pMPH has been constructed, which can produce the HBV polymerase fused with maltose binding protein and histidine tag (see FIG. 1).

To express the recombinant polymerase, microorganism is transformed with the expression vector pMPH so as to prepare transformant. The microorganism mentioned above contains all kinds of *Escherichia coli* which is suitable for the expression of recombinant proteins.

Particularly, *E. coli* NM522 strain was transformed with the expression vector pMPH and the transformant has been deposited with Korean Culture Center of Microorganism, Seoul, Korea, on Jul. 19, 1996 (Accession number: KCCM-10084).

The present invention provides a process for preparaing the recombinant HBV polymerase massively. *E. coli* transformant containing the expression vector is induced to express the recombinant protein and disrupted to obtain crude extract, then the HBV polymerase is purified by using histidine tag affinity column chromatography and other chromatographies.

Precisely, since the *E. coli* transformant containing the expression vector pMPH produces the recombinant HBV polymerase fused with MBP at the N-terminus, the HBV polymerase is purified as a form of fusion protein by using amylose resin column. And the histidine tagged polymerase only can be obtained separating MBP by treating protease factor Xa and the like.

In additon, the histidine tagged HBV polymerase is purified highly and conveniently by performing the metal chelating affinity column as histidine tag affinity column. The histidine tag maintains enzyme activity of the recombinant HBV polymerase during the purification process since it prevents protein degradation as well as facilitates the purification process of the HBV polymerase.

The present invention provides the RNase H enzyme derived from HBV polymerase.

Since human HBV polymerase has a RNase H domain with enzyme activity at the N-terminus, the RNase H domain of the present invention is prepared by inserting 3'-terminus of the HBV polymerase gene into a expression vector and inducing *E. coli* transformant.

The present invention provides expression vectors which produces the RNase H enzyme fused with MBP to prepare the RNase H enzyme derived from the HBV polymerase.

Figure 3:
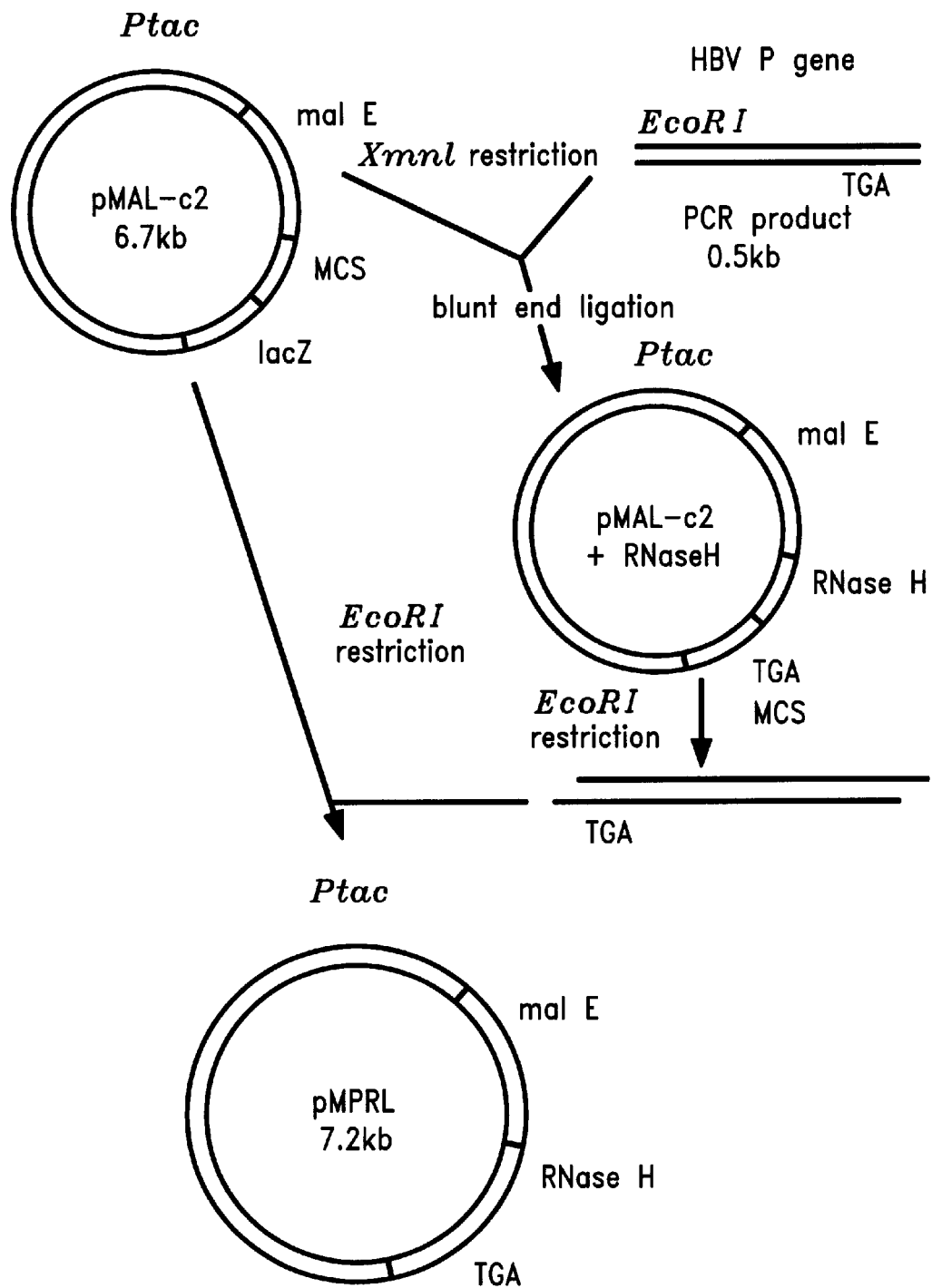
FIG. 3 depicts a strategy for constructing the expression vector PMPRL which produces the RNase H enzyme derived from the HBV polymerase.

Precisely, the RNase H subdomain gene of the HBV polymerase can be obtained by performing polymerase chain reaction (PCR) which utilizes oligonucleotides of SEQ ID. NO: 2 and SEQ ID. NO: 3 as primers (see Sequence Listing) and the expression vecor pMPLX already established as a template. The expression vector pMPLX can produce the HBV polymerase as a form fused with MBP (Korean Patent Application 94-3918). RNase H enzyme gene obtained above has been inserted into the plasmid vector pMAL-c2 to construct the expression vector pMPRL (see FIG. 3).

Particularly, *E. coli* NM522 strain was transformed with the expression vector pMRH and the transformant has been deposited with Korean Culture Center of Microorganism, Seoul, Korea, on Nov. 29, 1996 (Accession number: KCCM-10092).

In addition, the present invention provides expression vectors which produces RNase H enzyme fused with MBP and histidine tag in order to prepare the RNase H enzyme derived from the HBV polymerase.

Figure 4:
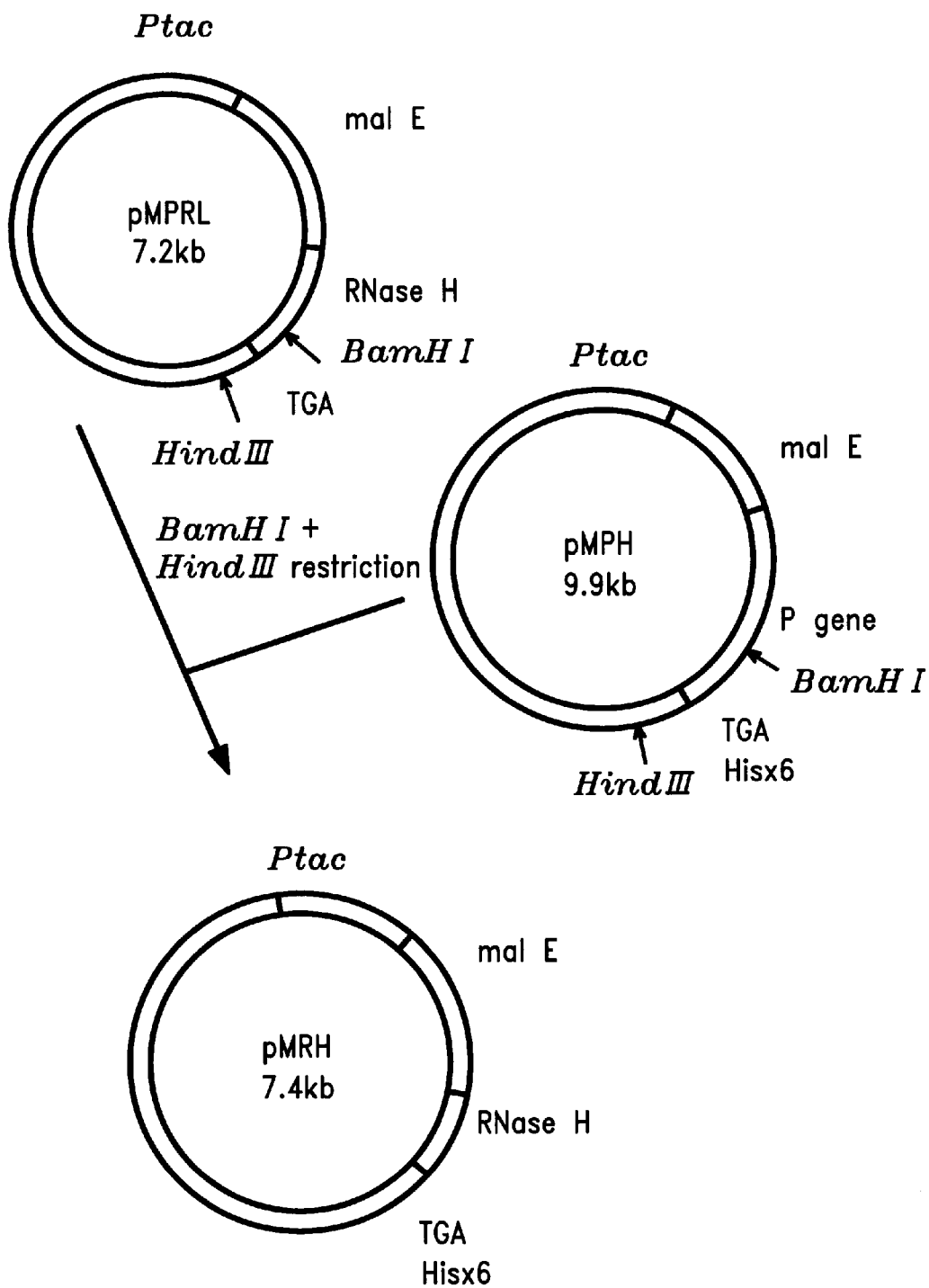
FIG. 4 depicts a strategy for constructing the expression vector pMRH which produces the active histidine-tagged RNase H enzyme derived from human HBV polymerase.

Precisely, the gene fragment of the HBV polymerase containing nucleotide sequences of histidine tag is obtained from the expression vector pMPH and inserted into the expression vector PMPRL to construct the expression vector pMRH (see FIG. 4).

Particularly, *E. coli* NM522 strain was transformed with the expression vector pMRH and the transformant has been deposited with Korean Culture Center of Microorganism, Seoul, Korea, on Nov. 11, 1996 (Accession number KCCM-10091).

The present invention provides a process for preparing the RNase H enzyme derived from the HBV polymerase by utilizing the expression vectors and the transformants describe above.

Precisely in order to purify the RNase H domain of the HBV polymerase, *E. coli* transformant containing the expression vector is induced for the protein expression, disrupted to obtain crude extracts, then RNase H enzyme as a form of fusion protein is purified by using amylose resin and maltose-containing buffer. And the histidine tagged RNase H enzyme only can be obtained separating MBP by treating protease factor Xa and the like. And the histidine tagged RNase H enzyme is purified higherly by performing histidine tag affinity column chromatography as the same process described above.

Molecular weights and purity of the HBV polymerase and the RNase H enzyme purified above have been determined by using SDS-polyacrylamide gel electrophoresis and western blotting. As a result, the HBV polymerase and the RNase H enzyme of the present invention is identified to be intact forms which has not been degraded (see FIG. 2, FIG. 5 and FIG. 6).

And reverse transcriptase activity in the HBV polymerase of the present invention has been examined. As a result, the recombinant polymerase with MBP and histidine tag has shown higher activity of reverse transcriptase than the polymerase without histidine tag. In detail, activities of DNA dependent DNA polymerase (DDDP) and RNA dependent DNA polymerase (RDDP) have been 19 times higher in histidine tagged form than those in intact form (see Table 1).

Precisely, in order to investigate RNA degradation by the RNase H activity, RNA/DNA complex is used as a substrate for the enzyme reaction. As a DNA template for preparing RNA/DNA complex, the plasmid pBS-oligo derived from the plamid pBS is selected, digested within restriction site SmaI, 102 nucleotides downstream from T7 promoter and then in vitro translation has been performed by using T7 RNA polymerase, radioactive nucleotides and so on. And RNA of 102 nucleotides is obtained by using QIAquick nucleotide removal kit, QIAGEN and synthetic DNA oligonucleotide (43-mer) of SEQ ID NO: 4 is added to prepare RNA/DNA complex which is shown in FIG. 7 (see Sequence Listing).

In order to measure the RNase H enzyme activity, radioactive RNA/DNA complex is reacted with the RNase H enzyme and the radioactivity in the supernatant of the reaction mixture is measured by using scintillation cocktail and the like. At that time maltose binding protein as a contrast sample, crude extract fraction, commercially available reverse transcriptase of Moloney murine Leukemia Virus as a comparative sample and so on are utilized. As a result, RNase H enzyme of the present invention is more active than that of reverse transcriptase of Moloney murine Leukemia Virus, approximately 90% activity (see FIG. 8).

In order to examine the enzymatic properties of the RNase H domain, the RNase H activity is measured in various reaction conditions by using proper buffers and radioactive RNA/DNA complex.

As results, the enzyme activity of the RNase H domain increases according to the enzyme amount (see FIG. 9) and takes about 3 hours of the reaction period to be shown (see FIG. 10). And preferably the temperature range is 32–42° C. for the enzymatic reaction (see FIG. 11) and pH range is broad comparatively such as 7.5–8.8 (see FIG. 12). And preferably the reaction mixture for the enzymatic reaction should have 20–100 mM range of KCl concentration (see FIG. 13), 4–8 mM range of magnesium concentration (see FIG. 14), and 4–12 mM range of manganese concentration (see FIG. 15).

More preferably, for the enzymatic reaction of the RNase H optimun temperature is 37° C., optimum pH is 7.9, optimum NaCl concentration is 40 mM, magnesium ion is 4 mM and manganese ion is 8 mM.

And the present invention provides uses of the HBV polymerase and the RNase H enzyme derived from the HBV polymerase for screening antiviral agents.

In order to select HBV inhibitors working at the multiplication stage of HBV by using the HBV polymerase,
(a) the HBV polymerase is reacted with homopolymer template, radioactive nucleotide and antiviral agent,
(b) the reaction solution of (a) stage is adsorpted onto anion adsorption filter and dried,
(c) the radioactivity of the adsorbent filter is measured by using scintillation cocktail and,
(d) the results of (c) stage is compared with those of comparative sample which does not contain a antiviral agent in the reaction mixture and used to calculate the inhibitory effects of HBV multiplcation.

Then poly(da)/oligo(dT)$_{12-18}$ is used as homopolymer template for DDDP activity and poly(rA)/oligo(dT)$_{12-18}$ for RDDP activity preferably and DE-81 anion adsorbent filter is used preferably.

In addition, in order to select antiviral agents by using the RNase H enzyme derived from the HBV polymerase, at first, enzyme substrates should be prepared by the process described below and then the radioactivity of the substrate should be measured.

In order to select HBV inhibitors working at the multiplication stage of HBV by using the RNase H domain of the HBV polymerase,
(a) the RNase H enzyme is reacted with the reaction substrate and antiviral agent,
(b) ammonium acetate is added to stop the reaction of (a) stage and precipitated by adding ethanol and centrifuging,
(c) the radioactivity of the supernatant of the precipitate is measured and,
(d) the results of (c) stage is compared with those of comparative sample which does not contain an antiviral agent in the reaction mixture and used to calculate the inhibitory effects of HBV multiplication.

Practical and presently preferred embodiments of the present invention are illustrative as shown in the following Examples.

However, it will be appreciated that those skilled in the art, on consideration of this disclosure, may make modification and improvements within the spirit and scope of the present invention.

EXAMPLES

Example 1

Construction of the expression vector pMPH

In order to construct the expression vector pMPH, the nucleotide sequence of 6 histidine residues was inserted into the 3'-terminus of HBV polymerase gene of the expression vector pMPLX already established (Korean Patent Application 94-3918) by site-specific insertion mutagenesis.

The E. coli CJ 236 strain (ung-, dut-) was transformed by the expression vector PMPLX, cultured until OD$_{600}$ was 0.3, and then infected with M13 K07 helper phage. After 1 hour, kanamycin was added into the growing culture and after culturing overnight, DNA containing uracil was obtained. The mutant expression vector containing 6 histidine residues, (His)$_6$ tag, was constructed by performing in vitro DNA polymerization, which used the primer for mutagenesis having nucleotide sequence of SEQ ID. NO: 1 (see Sequence Listing) and the above single-stranded DNA according to the Kunkel's method (Kunkel, T. A., Proc. Natl. Acad. Sci., 82: 488, 1985). The mutant expression vector described above was selected by using the restriction enzyme EcoRI site inserted and DNA sequence analysis.

Particularly, the primer for mutagenesis was prepared to have 6 histidine codons directly upstream of the stop codon in the open reading frame of HBV polymerase gene. Thus the histidine tag was inserted without any sequence change in HBV polymerase gene. In addition, the EcoRI site (GAATTC) which lacked in the expression vector pMPLX was introduced directly downstream of the stop codon, thus the mutant expression vector and the transformant can be easily selected. The mutant expression vector can be have the right open reading frame and expression direction, which is examined by the analysis of DNA sequence.

Figure 1:
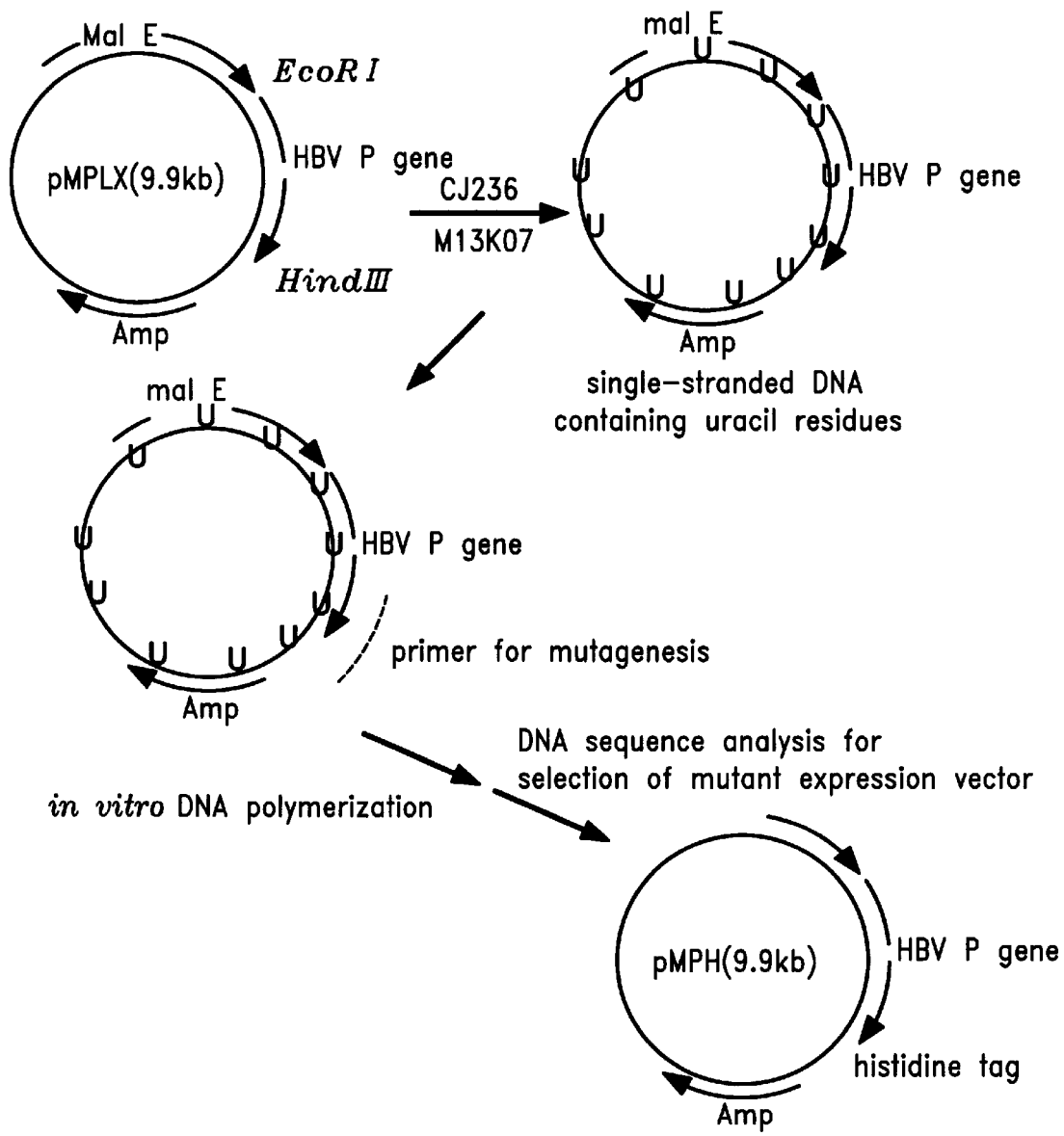
FIG. 1 depicts a strategy for constructing the expression vector pMPH which produces the HBV polymerase containing a histidine tag.

As a result, the expression vector PMPH of the present invention which can produce the recombinant protein, the HBV polymerase fused with MBP and histidine tag was constructed (see FIG. 1).

Example 2

Expression of the HBV polymerase

In order to obtain a large amount of HBV polymerase, E. coli NM 522 strain was transformed with the expression vector pMPH which can produce the recombinant protein, the HBV polymerase fused with MBP and histidine tag.

The transformant described above was inoculated into 3 ml of 2× YT medium, cultured for 16–20 hours and the growing culture was diluted 1:100 and again inoculated into 400 ml of LB medium. Then the growing culture was incubated at 37° C. until OD$_{600}$ reached 0.5, isopropylthiogalactoside (IPTG) was added into the E. coli culture and again cultured at 26–37° C. for 6–18 hours.

Example 3

Purification of the HBV polymerase

In order to purify the HBV polymerase, the E. coli culture which was induced for the expression in Example 2 was centrifuged for 20 minutes at 4,000 rpm. The cell pellet was resuspended in 5 ml of buffer A (10 mM Tris-Cl, pH 7.4, 200 mM NaCl, 1 mM EDTA) and disrupted by sonication for 20 seconds 5 times. To separate the HBV polymerase by using MBP, the crude extract was centrifuged and the supernatant was loaded into amylose resin column (New England Biolab.) of which the resin was washed with buffer A, 50 times volume of the supernatant volume. The HBV polymerase fused with MBP was eluted by using buffer A containing 10 mM maltose.

In addition, in order to purify HBV polymerase highly by using the histidine tag, the protein fraction obtained above as again loaded into $Ni^{2+}$-NTA resin (QIAGEN). After the loaded protein sample passed the column, buffer B with 10 times volume of the resin volume (50 mM $Na_2HPO_4$, 300 mM NaCl, 10% glycerol, 10 mM imidazole, pH 6.0) containing 10 mM imidazole was used to wash the column and then buffer B with 30 times volume of the resin volume is used to wash the column. The HBV polymerase was eluted and purified by using 10–200 mM concentration gradient of imidazole.

Example 4
Identification of molecular weight and purity of the HBV polymerase In order to identify molecular weight and purity of the HBV polymerase which was obtained in Example 3, the purified HBV polymerase was electrophoresed on SDS-polyacrylamide gel according to the Laemmli's method and western blotting was also performed, and the amount of HBV polymerase was quantified according to Bradford's method.

The $^{MRGS}$His-Ag which can bind histidine-tagged protein was used for western blot analysis. The $^{MRGS}$His-Ag (QIAGEN) which was diluted at the ratio of 1:2,000 was used as a first antigen and the rabbit anti-mouse IgG (Sigma) at the ratio of 1:16,000 was used as a second antigen.

Figures 2A, 2B:
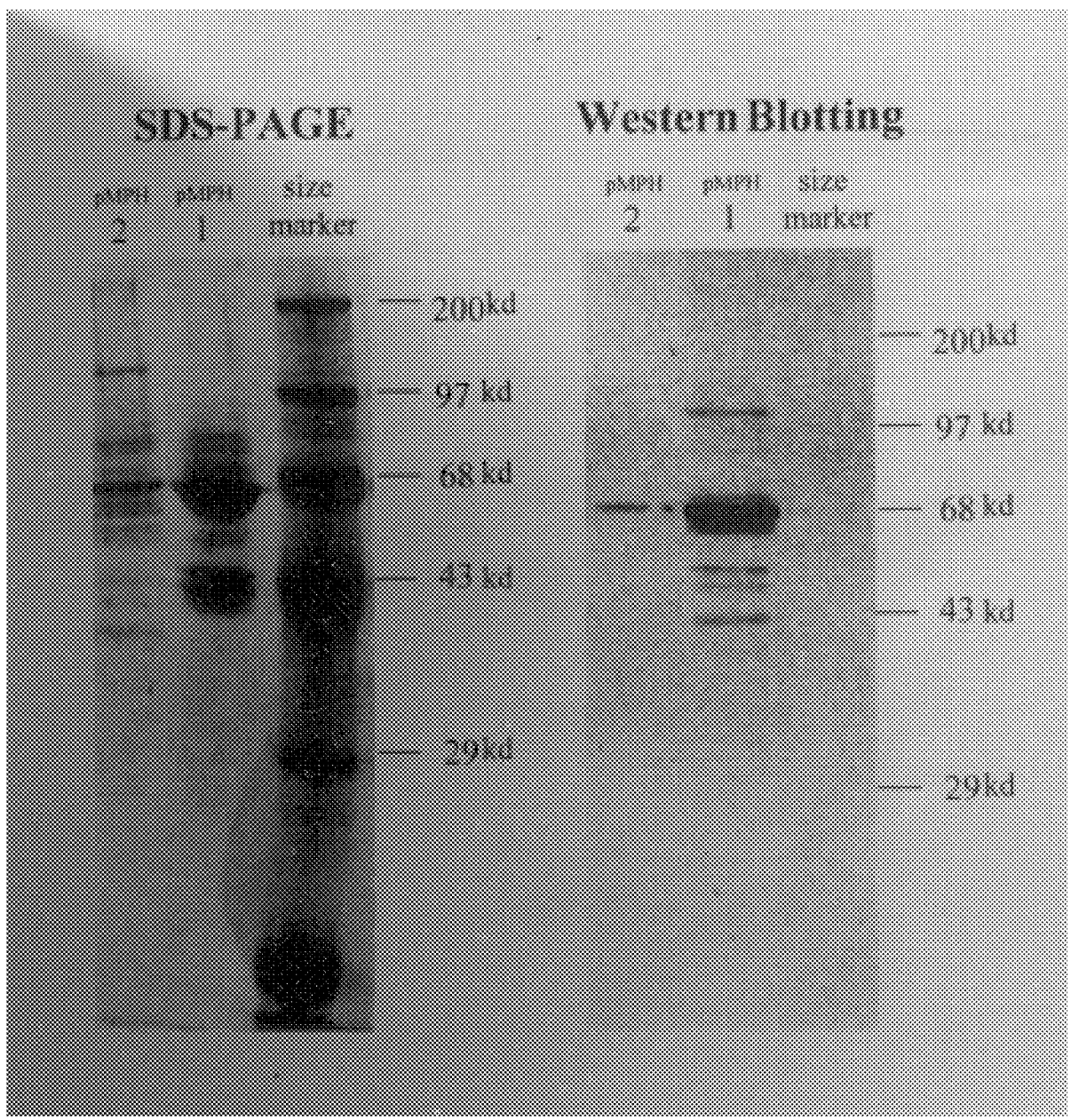
FIG. 2 depicts the HBV polymerase which has been produced and purified from *E. coli* NM 522/pMPH transformant by SDS-polyacrylamide gel electrophoresis.

As a result, HBV polymerase of the present invention containing a histidine tag was identified to have 144 KD protein size onto SDS-polyacrylamide gel, which was not detected in the case of the HBV polymerase already purified due to hydrolysis of the protein (see FIG. 2). The expressed protein concentration was 400 µg/l, which was similar to already purified HBV polymerase.

Example 5
Identification of the HBV polymerase activity

In order to identify the activity of the recombinant HBV polymerase purified in the above process, the recombinant HBV polymerase was electrophoresed on the 7.5% SDS-polyacrylamide gel containing substrate (4.5% stacking gel). After the electrophoresis, the gel was soaked in renaturation buffer solution (50 mM Tris-Cl, pH 7.4) and incubated at 4° C. for 24 hours with shaking.

The renaturated gel by removing SDS was mixed with 100 ml of reaction solution (50 mM Tris-Cl, pH 7.4, 5 mM dithiotreitol, 5 mM $MgCl_2$, 0.01% NP-40, 10 mM dGTP, 10 mM dATP, 10 mM dCTP, 20 µCi $^{32}$P-dTTP) and the reaction mixture was incubated at 37° C for 16 hours. Then 500 ml 5% of TCA-1% $Na_4P_2O_7$ was added into the reaction mixture described above and the gel was washed at 4° C. for 20 hours and the dried gel was exposed onto X-ray film.

As a result, the 144 KD protein which is putative HBV polymerase fused with MBP and histidine tag showed reverse transcriptase activity. In addition, the reverse transcriptase activity of the HBV polymerase with histidine tag is more active than HBV polymerase without histidine tag.

Example 6
Assay of the HBV polymerase activity

In order to assay the activity of HBV polymerase purified at above process, the reaction mixture containing 0.5 µg the purified HBV polymerase, standard polymerase reaction buffer, 50 ng homopolymer template, and 2 µCi $^{32}$P-d TTP (~3000 Ci/mmol) was incubated at 37° C. for 1 hour. The poly(dA)/oligo $(dT)_{12-18}$ was used as a template in the assay of the DDDP activity and the poly $(rA)$/oligo $(dT)_{12-18}$ was used as a template in the assay of the RDDP activity. This reaction mixture was adsorbed onto a disk filter and the disk filter was washed and mixed with scintillation cocktail (5.5 g/l PPO, 0.15 g/l POPOP) to measure the radioactivity of $^{32}$P-dTTP by using liquid scintillation counter.

As a result, the HBV polymerase containing a histidine tag of the present invention showed relatively higher specific activity (cpm/µg) of DDDP and RDDP than the activity of the polymerase already purified. Particularly, the DDDP activity of the recombinant HBV polymerase produced by the expression vector of the present invention was 19 times higher than the already purified polymerase and the RDDP activity of the recombinant HBV polymerase produced by expression vector of the present invention was 5.6 times higher than the already purified polymerase (see Table 1).

TABLE 1

Comparison of the enzyme activity of recombinant HBV polymerase

|  |  | pMPLX | pMPH | |
|---|---|---|---|---|
|  |  | amylose column | amylose column | Ni-NTA column |
| DDDP | C.P.M. specific activity | 12,757 1 | 44,134 3.4 | 239,850 18.8 |
| RDDP | C.P.M. specific activity | 11,689 1 | 32,713 2.79 | 65,935 5.64 |

Example 7
Constuction of the expression vector pMPRL

In order to construct the expression vector pMPRL which produces RNase H enzyme derived from HBV polymerase, the gene fraction of the 3'-terminus HBV polymerase gene encoding RNase. H domain (subdomain) was amplified by PCR. The 5'-terminal primer has the sequence of SEQ ID. NO: 2 and 3'-terminal primer has the sequence of SEQ ID. NO: 3 (see Sequence Listing). The expression vector pMPLX (Korean Patent Application 94-3918) was used as a DNA template. The size of the DNA fraction amplified was identifieed to be 0.5 kb. The above DNA fraction was cut by XmnI restriction enzyme site and ligated with the plasmid pMAL-c2. The ligation product was cut by restriction enzyme EcoRI, so the DNA fraction which corresponds to RNase H enzyme was separated. The above DNA fraction was ligated with the plasmid pMAL-c2 cut with EcoRI restriction enzyme, and finally the expression vector pMPRL of 7.2 kb size was constructed (see FIG. 3). The open reading frame of MBP gene of the plasmid pMAL-c2 and the RNase H gene was connected correctly, which was identified by the sequence analysis of the ligated EcoRI site.

Example 8
Construction of the expression vector pMRH

In order to construct the expression vector pMRH =which produces RNase H domain derived from HBV polymerase containing a histidine tag, the expression vector pMPH which produces HBV polymerase containing a histidine tag was used. The expression vector pMPH was cut by restriction enzyme BamHI and HindIII, so the DNA fraction which contains DNA sequence encoding a histidine tag was obtained. After the expression vector PMPRL which was constructed in Example 7 to produce RNase H enzyme, was cut by restriction enzyme BamHI and HindIII, the DNA sequence encoding a histidine tag was inserted into the above expression vector pMPRH. As a result, the expression vector pMRH was constructed which produces the recombinant protein, the RNase H domain fused with MBP and histidine tag at the C-terminus (see FIG. 4).

Example 9
Expression of the RNase H domain derived from human HBV polymerase

RNase H domain derived from HBV polymerase was expressed in E. coli by using the expression vector PMPRL and pMRH. E. coli NM 522 was transformed by the expression vector pMRH and pMPRL respectively and the transformants were cultured overnight in 2× YT medium, overnight. This growing cultures were diluted 1:100, inoculated into a glucose rich medium and incubated until $OD_{600}$ reached 0.5. And then IPTG was added into the medium of which the final concentration was 0.5 mM. The above growing cultures were incubated again at 23° C. for 12 hours and the RNase H domain was expressed.

The above cultured broth was centrifuged for 10 minutes at 3,000 rpm and the cell pellet was washed with 10 ml of column buffer (10 mM Tris-Cl, pH 7.4, 200 mM NaCl, 1 mM EDTA), centrifuged again and resuspended. The cells were freezed and thawed 4 times repeatedly, and then disrupted by sonication for 10 seconds 3 times. The crude extract prepared in the above process was centrifuged for 30 minutes at 13,000 rpm, 4° C. and the supernatant was separated. The above process was repeated 3 times and then the supernatant passed the amylose resin. The column was washed by using column buffer with 50 times of resin volume, and the RNase H domain was eluted by using buffer containing 10 mM maltose. The purified recombinant protein was hydrolyzed into MBP and the RNase H domain by treating protease factor Xa.

In addition, the RNase H domain produced from the expression vector pMRH of the present invention was purified by using histidine tag affinity column, because RNase H has a histidine tag at the C-terminus. The resin (Ni-NTA, QIAGEN) used in the the histidine tag affinity column was activated by using sonication buffer (50 mM sodium phosphate, pH 8.0, 300 mM sodium chloride) and 4–5 ml of the activated resin charged the glass tube whose diameter was about 1 cm. The protein sample obtained from above description passed the resin at the 0.1 ml/min flow rate and the column was washed by using washing buffer with the 100–200 times volume of protein sample (50 mM sodium phosphate, pH 6.0, 300 mM sodium chloride, 10% glycerol). The recombinant protein was eluted by washing the column with concentration gradient of 0.01–0.5 M imidazole.

As a result, the active RNase H domain was separated from the histidine tag affinity column at 50 mM concentration of imidazole. The purified RNase H domain derived from human HBV polymerase was identified by performing SDS-PAGE and western blotting (see FIG. 5 and FIG. 6).

Example 10
Preparation of the substrate of the RNase H enzyme

In order to identify the RNase H activity of the present invention, RNA/DNA complex which can be used as a substrate of the RNase H enzyme was preprared by performing in vitro transcription with T7 RNA polymerase. The template used in the preparation of run-off transcript was the plasmid pBS-oligo derived from the plasmid pBS. E. coli was transformed with the plasmid pBS-oligo, and the transformant was cultured massively to obtain large amount of the plasmid pBS-oligo by using the alkaline lysis method. The restriction enzyme SmaI site .is located in the 102 nucleotides downstream of T7 promoter of the plasmid pBS-oligo.

The plasmid pBS-oligo was cut with restriction enzyme SmaI, electrophoresed on 0.7% agarose gel, eluted from the gel, and used to perform in virto transcription. The in vitro transcription was performed by using the reaction mixture which is composed of 30 μl distilled water, 20 μl 5× reaction buffer (200 mM Tris-Cl, pH 7.5, 30 mM magnesium chloride, 10 mM spermidine, 50 mM sodium chloride), 10 μl dithiotreitol, 10 μl solution containing 2–5 μg the plasmid pBS-oligo cut with restriction enzyme SmaI, 5 μl 2.5 mM ATP, 5 μl 2.5 mM GTP, 5 μl 2.5 mM UTP, 5 μl 0.1 mM CTP, 3 μl RNasin, 5 μl[$^{32}$P] CTP 50 μCi, 2 μl T7 RNA polymerase. The total reaction volume was adjusted 100 μl, and the above reaction mixture was incubated for 1–2 hours at 37° C. Then the RNA produced which is 102 nucleotides long was separated by using QIAquick nucleotide removal kit (QIAGEN), electrophoresed with 1–5 μl on 8 M urea-6% TBE gel, and then the gel was dried, exposed onto X-ray film for more than 48 hours. The X-ray film wags developed to examine the radioactive signal.

The 102 nucleotides RNA whose radioactive signal was idientified was mixed with the same mole of synthetic DNA oligomer (43-mer) which has DNA sequence of SEQ ID. NO: 4, heated at 70–80° C., for 3–10 minutes, and then cooled at room temperature. Finally RNA/DNA complex which had radioactive signal was prepared by above process whose structure of RNA/DNA complex is shown in FIG. 7.

Example 11
Identification of the RNase H activity

The RNase H activity was identified by using the RNase H enzyme purified in Example 9 and RNA/DNA complex with radioactive signal prepared in Example 10. In order to identify the RNase H activity of the present invention, 1 μg of RNase H enzyme of the present invention was mixed with 40 mM Tris-Cl (pH 7.9), 4 mM magnesium chloride, 40 mM potassium chloride and RNA/DNA complex, and the above reaction mixture was incubated at 37° C. for 3 hours, and then the reaction was stopped by adding-50 mM EDTA to the reaction mixture. To the small volume of the reaction solution the same amount of 10% ice-cold TCA was added. The above reaction mixture was incubated at 4° C. for 1 hour and centrifuged for 15 minutes at 4° C., 13,000 rpm. The supernatant was obtained and the radioactive signal of the 20 μl of supernatant was measured by using scintillation cocktail.

As a control, MBP which was fused with the RNase H domain was reacted in the same condition, but the radioactive signal was not detected. In addition, the activity of the RNase H activities of the following proteins was compared in the same condition with one another, and the following proteins consisted in crude extract obtained from Example 9, the commercially available reverse transcriptase of the Moloney murine Leukemia Virus, RNase H enzyme purified by amylose column after expression from the expression vector pMPRL, RNase H enzyme purified primarily by amylose column and secondarily by histidine tag affinity column after expression from the expression vector pMRH. As a result, the activity of RNase H domain was 90% of the

13 activity of RNase H which consists in the commercially available reverse transcriptase of the Moloney murine Leukemia Virus (see FIG. 8).

Example 12
Variation of the RNase H activity according to the amount of RNase H enzyme In order to measure the variation of the RNase H activity according to the reaction condition, the reaction condition of the RNase H enzyme was changed and the activity of the RNase H enzyme was measured. In detail, as the amount changed from 0 to 1.6 μg, the RNase H enzyme of the present invention was mixed with 40 mM Tris-Cl (pH 7.9), 4 mM magnesium chloride, 40 mM potassium chloride, and 30,000 cpm RNA/DNA complex and the reaction mixture was incubated at 37° C. for 3 hours. As a result, the RNase H enzyme activity became higher, as the amount of the enzyme increases (see FIG. 9).

Example 13
Variation of the RNase H activity accoding to the reaction period 1 μg of the RNase H enzyme was mixed with 40 mM Tris-Cl (pH 7.9), 4 mM magnesium chloride, 40 mM potassium chloride and 30,000 cpm RNA/DNA complex, and the reaction mixture was incubated at 37° C. as described in Example 11, and the reaction period showing the enzyme activity sufficiently was measured. It took about 3 hours for the RNase H enzyme to be active (see FIG. 10).

Example 14
Variation of the RNase H activity according to the reaction temperature As the temperature was varied from 0 to 52° C., 1 μg of the RNase H enzyme was mixed with 40 mM Tris-Cl (pH 7.9), 4 mM magnesium chloride, 40 mM potassium chloride, and 30,000 cpm RNA/DNA complex, and the reaction mixture was incubated for 3 hours as described in Example 11.

As a result, the RNase H activity was identified at relatively broad range of 32–42° C. (see FIG. 11).

Example 15
Variation of the RNase H activity to the pH of the reaction solution As the pH was changed from pH 6.0 to pH 10.0, 1 μg of RNase H enzyme was mixed with 40 mM Tris-Cl, 4 mM magnesium chloride, 40 mM potassium chloride and 30,000 cpm RNA/DNA complex and the reaction mixture was incubated at 37° C. for 3 hours, as described in Example 11. The RNase H activity had the highest value at the pH range of 7.5–8.8 (see FIG. 12).

Example 16
Variation of the RNase H activity according to the concentration of potassium chloride As the concentration of potassium chloride was changed, from 0 to 400 mM, 1 μg of RNase H enzyme was mixed with 40 mM Tris-Cl (pH 7.9), 4 mM magnesium chloride and 30,000 cpm RNA/DNA complex and the reaction mixture was incubated at 37° C. for 3 hours as described in Example 11. The RNase H activity had the highest value when the concentration of potassium chloride was 20–100 mM (see FIG. 13).

14

Example 17
Variation of the RNase H activity according to the concentration of magnesium ion As the concentration of magnesium ion ($Mg^{2+}$) was changed from 0 to 50 mM, 1 μg of RNase H enzyme was mixed with 40 mM Tris-Cl (pH 7.9), 40 mM potassium chloride and 30,000 cpm RNA/DNA complex and the reaction mixture was incubated at 37° C., for 3 hours, as described in Example 11. The RNase H activity had the highest value when the concentration of magnesium ion was 4 to 8 mM (see FIG. 14).

Example 18
Variation of the RNase H activity according to the concentration of manganese ion As the cation (II) of the reaction solution was substituted with manganese ion ($Mn^{2+}$), 1 μg of RNase H enzyme was mixed with 40 mM Tris-Cl (pH 7.9), 40 mM potassium chloride and 30,000 cpm RNA/DNA complex and the reaction mixture was incubated at 37° C. for 3 hours, as described in Example 11. The RNase H activity had the highest value when the concentration of manganese ion is 4 to 12 mM (see FIG. 15).

Example 19
Screening of HBV antiviral agents using HBV polymerase

By using the HBV polymerase of the present invention, the following reaction was performed in order to screen antiviral agents. 50 μl of the reaction mixture consisting in 0.5 μg of the purified HBV polymerase, 50 mM Tris-Cl, pH 7.4, 50 mM potassium chloride, 0.5 mM manganese chloride, 1 mM dithiothreitol, 0.01% NP-40, 50 ng homopolymer template (RDDP poly (rA)/oligo $(dT)_{12-18}$ DDDP: poly (dA)/oligo (dT) $_{12-18}$) and 2 μCi [α-$^{32}$P] TTP (3,000 Ci/mmol) respectively was incubated at 37° C. for 1 hour. Then, the reaction solution was precipitated by TCA and adsorbed onto DE-81 anion adsorbent filter. The adsorbent filter containing the sample was washed with 0.1 M phosphate buffer, and the washed filter was dried with infrared rays. Then after mixing with scintillation cocktail the RNase H activity was assayed by measuring radioactivity (cpm).

In order to select the antiviral agents by using the above process, 10 μl of putative antiviral agents was added into the above reaction mixture, and the antiviral activity was measured and compared with the enzyme activity of the reaction sample which didn't contain antiviral agents.

Example 20
Screening of HBV antiviral agents using the RNase H enzyme

By using the RNase H enzyme of the present invention, a enzyme substrate was prepared by the following process in order to screen antiviral agents.

In order to prepare RNA transcript, single-stranded DNA of M13 phage was purified and transcribed by *E. coli* RNA polymerase. The following reaction mixture of 4 μl buffer solution (200 mM Tris-Cl, pH 7.5, 30 mM magnesium chloride, 10 mM spermidine and 50 mM sodium chloride), 2 μl 100 mM dithiothreitol, 1 μl RNasin (Promega), 1 μl 2.5 mM ATP, 1 μl 2.5 mM GTP, 1 μl 2.5 mM UTP, 0.6 μl distilled water without RNase, 2.4 μl 0.1 mM CTP, 1 μl single-stranded DNA of M13mp19 (about 1 μg/μl) and 5 μl [α-$^{32}$P] CTP (10 μCi/μl, Amersham) were incubated at 37° C. for 15 hours with 1 μl of *E. coli* RNA polymerase (Promaga). The above reaction mixture passed Sephadex G-50 column so as to remove the nucleic acids remained. The volume of reaction solution which passed the above column was measured and 0.5× volume of 7.5 M ammonium acetate and 2× volume of ethanol were added into the above reaction mixture and precipitated at −20° C. for 1 hour. The RNA transcript precipitated above was obtained by centrifuging and washing with 70% ethanol. Then RNA transcript was resuspended in 100 μl of 10 mM Tris-Cl, pH 8.0 and the radioactive signal of 1 μl of RNA transcript solution was measured.

In addition, RNA transcript which was obtained by the above process and single-stranded DNA of M13mp19 suspended in buffer solution (10 mM Tris-Cl, pH 8.0, 1 mM EDTA, 80 mM potassium chloride) were heated in same amounts at 85° C. for 2 minutes, and then the above reaction mixture was cooled at room temperature. As a result, RNA/DNA complex was obtained by precipitating with ethanol and suspended in 100 μl of TE buffer (pH 8.0).

In order to measure the above RNase H activity, 50 μl of the reaction mixture consisting in 25 μl of 2× buffer solution (40 mM Tris-Cl, pH 8.0, 20 mM potassium chloride, 2 mM magnesium chloride, 4 mM dithiothreitol), 5 μl RNase H domain, 5 μl enzyme substrate (about 50,000 cpm) and 15 μl distilled water was prepared and incubated at 37° C. for 30 minutes. The reaction was stopped by using 2 5μl of 7.5 M ammonium acetate and precipitated by using 230 μl of ethanol. In order to measure antiviral activities, 5 μl of antiviral agents was added to the above reaction mixture and the antiviral activity was measured and compared with the enzyme activity of RNase H of the reaction sample which didn't contain antiviral agents.

As illustrated in the above description, highly active HBV polymerase can be produced massively in *E. coli* because HBV polymerase of the present invention is stable due to its histidine tag. And HBV polymerase of the present invention can be easily purified by using histidine tag affinity column chromatography. Precisely, the HBV polymerase shows highly specific activity such as 5–20 times higher activity than the polymerase already purified since it can be purified doubly by exploiting MBP and histidine tag. And the RNase H enzyme derived from HBV polymerase can be also produced massively in *E. coli*, and purified easily. Furthermore, the RNase H activity is maintained highly during the purification process.

Therefore, the HBV polymerase and its RNase H domain of the present invention can be used to select various antiviral agents effectively. And the antiviral agents which is selected by the screening methods of the present invention can be used to understand the mechanism of HBV replication and to treat hepatitis, liver cirrhosis, and liver cancer caused by HBV infection.

What is claimed is:

1. A RNase H enzyme derived from human HBV polymerase.

2. The RNase H enzyme according to claim 1, which is fused with maltose binding protein.

3. The RNase H enzyme according to claim 2, which contains a histidine tag at the C-terminus.

4. The RNase H enzyme according to claim 1, which is active at 32–42° C., at the pH range of 7.5–8.8, in reaction solution containing potassium chloride 20–100 mM, magnesium ion 4–8 mM or manganese ion 4–12 mM.

5. The expression vector pMPRL which produces the RNase H enzyme of claim 2.

6. The *E. coli* transformant which is prepared by transforming host cells with the expression vector pMPRL of claim 5 (KCCM-10092).

7. The expression vector pMRH which produces the RNase H enzyme of claim 3.

8. The *E. coli* transformant which is prepared by transforming host cells with the expression vector pMRH of claim 7 (KCCM-10091).

9. A process for preparing the RNase H enzyme of claim 1, comprising steps as follows: (a) inducing the expression of the RNase H enzyme after culturing the *E. coli* transformants of claim 6 or claim 8, (b) performing amylose affinity column chromatography with crude extract, (c) treating protease factor Xa.

10. The process for preparing RNase H enzyme of claim 1 according to claim 9, comprising a further step: performing histidine tag affinity column chromatography in the *E. coli* transformant of claim 8.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetic oligonucleotide"

(xi) SEQUENCE DESCRIPTION: SEQ ID NO:1:

GGAGACCACC GCATCACCAT CACCATCACT GAGAATTCAC GCCCATCAGG      50

(2) INFORMATION FOR SEQ ID NO:2:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetic oligonucleotide"

(xi) SEQUENCE DESCRIPTION: SEQ ID NO:2:

CCCCGTTGCC CGGGAATTCC GAACAGGTCT CTGCC      35

(2) INFORMATION FOR SEQ ID NO:3:

(i) SEQUENCE CHARACTERISTICS:
      (A) LENGTH: 18 base pairs
      (B) TYPE: nucleic acid
      (C) STRANDEDNESS: single
      (D) TOPOLOGY: linear -continued

```
(ii) MOLECULE TYPE: other nucleic acid
     (A) DESCRIPTION: /desc = "Synthetic oligonucleotide"

(xi) SEQUENCE DESCRIPTION: SEQ ID NO:3:

TCACGGTGGT CTCCATGC                                                    18

(2) INFORMATION FOR SEQ ID NO:4:

(i) SEQUENCE CHARACTERISTICS:
       (A) LENGTH: 43 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic oligonucleotide"

(xi) SEQUENCE DESCRIPTION: SEQ ID NO:4:

AATTGCGTGC GAGGCGATTG GTTTGGGGCC AGAGTGGGCC AGG                         43
```